United States Patent
Lechmann et al.

(10) Patent No.: US 10,085,851 B2
(45) Date of Patent: Oct. 2, 2018

(54) INTERVERTEBRAL PROSTHESIS OR DISK PROSTHESIS

(71) Applicant: DePuy Synthes Products, Inc., Raynham, MA (US)

(72) Inventors: Beat Lechmann, Grenchen (CH); Robert Frigg, Bettlach (CH); Roger Buerki, Balsthal (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/623,707

(22) Filed: Jun. 15, 2017

(65) Prior Publication Data

US 2017/0281362 A1    Oct. 5, 2017

Related U.S. Application Data

(63) Continuation of application No. 14/638,196, filed on Mar. 4, 2015, now Pat. No. 9,700,432, which is a
(Continued)

(51) Int. Cl.
*A61F 2/44*    (2006.01)
*A61F 2/30*    (2006.01)
*A61F 2/46*    (2006.01)

(52) U.S. Cl.
CPC .......... *A61F 2/447* (2013.01); *A61F 2/30771* (2013.01); *A61F 2/442* (2013.01);
(Continued)

(58) Field of Classification Search
CPC ............ A61F 2/4455; A61F 2002/4475; A61F 2002/2835; A61F 2002/30785
See application file for complete search history.

(56) References Cited

U.S. PATENT DOCUMENTS

| 4,338,925 A | 7/1982 | Miller |
| 4,405,249 A | 9/1983 | Scales |

(Continued)

FOREIGN PATENT DOCUMENTS

| DE | 197 10 392 C1 | 7/1999 |
| FR | 2 820 630 A1 | 8/2002 |

(Continued)

OTHER PUBLICATIONS

European Office Action for Application No. 04729392.3, dated Mar. 28, 2017 (7 pages).

(Continued)

*Primary Examiner* — Lynnsy Summitt
(74) *Attorney, Agent, or Firm* — Nutter McClennen & Fish LLP

(57) ABSTRACT

An intervertebral prosthesis or disk prosthesis comprising a front side, a rear side, an upper side which can be placed on the base plate of vertebral body, a lower side which can be placed on the base plate of a vertebral body, a right side, a left side, a cavity which can receive a fluid hydraulic osteocementum, an opening in the cavity and several outlets out from the cavity. The total of the transversal surfaces of the outlets $S_V$ on the front side, the total of the transversal surfaces of the outlets $S_H$ on the rear side, the total of the transversal surfaces of the outlets $S_R$ on the right side and the total of the transversal surfaces of the outlets on the left side satisfy the following conditions: $S_L > S_R$ or $S_R > S_L$ or $S_H > S_V$ or $S_V > S_H$.

18 Claims, 7 Drawing Sheets

Related U.S. Application Data continuation of application No. 11/587,723, filed as application No. PCT/CH2004/000250 on Apr. 26, 2004, now Pat. No. 8,992,618.

(52) U.S. Cl.
CPC .............. *A61F 2/446* (2013.01); *A61F 2/46* (2013.01); *A61F 2002/30777* (2013.01); *A61F 2002/30785* (2013.01); *A61F 2002/30789* (2013.01); *A61F 2002/30841* (2013.01); *A61F 2002/448* (2013.01); *A61F 2002/4475* (2013.01); *A61F 2002/4631* (2013.01); *A61F 2310/00353* (2013.01)

(56) References Cited

U.S. PATENT DOCUMENTS

| | | | |
|---|---|---|---|
| 4,736,738 A | 4/1988 | Lipovsek et al. |
| 4,863,476 A | 9/1989 | Shepperd |
| 5,123,926 A | 6/1992 | Pisharodi |
| 5,214,987 A | 6/1993 | Fenton, Sr. |
| 5,397,364 A | 3/1995 | Kozak et al. |
| 5,571,189 A | 11/1996 | Kuslich |
| 5,665,122 A | 9/1997 | Kambin |
| 5,669,909 A | 9/1997 | Zdeblick et al. |
| 5,697,932 A | 12/1997 | Smith et al. |
| 5,888,224 A | 3/1999 | Beckers et al. |
| 6,039,761 A | 3/2000 | Li et al. |
| 6,048,343 A | 4/2000 | Mathis et al. |
| 6,059,829 A | 5/2000 | Schlaphfer |
| 6,110,179 A | 8/2000 | Flivik et al. |
| 6,123,705 A | 9/2000 | Michelson |
| 6,176,882 B1 | 1/2001 | Biedermann et al. |
| 6,485,517 B1 | 11/2002 | Michelson |
| 6,645,213 B2 | 11/2003 | Sand et al. |
| 6,676,664 B1 | 1/2004 | Al-Assir |
| 6,726,722 B2 | 4/2004 | Walkenhorst et al. |
| 6,733,535 B2 | 5/2004 | Michelson |
| 6,923,810 B1 | 8/2005 | Michelson |
| 6,953,477 B2 | 10/2005 | Berry |
| 7,128,760 B2 | 10/2006 | Michelson |
| 7,156,877 B2 | 1/2007 | Lotz et al. |
| 7,316,689 B2 | 1/2008 | Lieberman |
| 7,361,193 B2 | 4/2008 | Frey et al. |
| 7,500,991 B2 | 3/2009 | Bartish, Jr. et al. |
| 7,591,852 B2 | 9/2009 | Prosser |
| 7,637,954 B2 | 12/2009 | Michelson |
| 7,655,027 B2 | 2/2010 | Michelson |
| 7,703,727 B2 | 4/2010 | Selness |
| 7,731,751 B2 | 6/2010 | Butler et al. |
| 7,799,081 B2 | 9/2010 | McKinley |
| 7,837,734 B2 | 11/2010 | Zucherman et al. |
| 7,850,733 B2 | 12/2010 | Baynham et al. |
| 8,002,833 B2 | 8/2011 | Fabris Monterumici et al. |
| 8,105,382 B2 | 1/2012 | Olmos et al. |
| 8,262,666 B2 | 9/2012 | Baynham et al. |
| 8,267,939 B2 | 9/2012 | Cipoletti et al. |
| 8,343,193 B2 | 1/2013 | Johnson et al. |
| 8,366,777 B2 | 2/2013 | Matthis et al. |
| 8,992,618 B2 | 3/2015 | Lechmann et al. |
| 9,408,719 B2 | 8/2016 | Lechmann et al. |
| 9,700,432 B2 | 7/2017 | Lechmann et al. |
| 2001/0005796 A1 | 6/2001 | Zdeblick et al. |
| 2001/0032018 A1 | 10/2001 | Castro et al. |
| 2002/0029082 A1* | 3/2002 | Muhanna .............. A61F 2/4455 623/17.11 |
| 2002/0058947 A1 | 5/2002 | Hochschuler et al. |
| 2002/0082700 A1 | 6/2002 | Bianchi et al. |
| 2002/0092871 A1 | 7/2002 | Rickard et al. |
| 2002/0147497 A1 | 10/2002 | Belef et al. |
| 2003/0036762 A1 | 2/2003 | Kerr et al. |
| 2003/0100950 A1 | 5/2003 | Moret |
| 2004/0010260 A1 | 1/2004 | Scribner et al. |
| 2004/0030389 A1 | 2/2004 | Ferree |
| 2004/0127993 A1 | 7/2004 | Kast et al. |
| 2004/0186572 A1 | 9/2004 | Lange et al. |
| 2005/0038513 A1 | 2/2005 | Michelson |
| 2005/0070900 A1 | 3/2005 | Serhan et al. |
| 2005/0119747 A1 | 6/2005 | Fabris Monterumici et al. |
| 2005/0149192 A1* | 7/2005 | Zucherman ........ A61B 17/1671 623/17.11 |
| 2005/0261781 A1* | 11/2005 | Sennett .............. A61B 17/7098 623/23.54 |
| 2006/0058878 A1 | 3/2006 | Michelson |
| 2006/0122701 A1 | 6/2006 | Kiester |
| 2007/0161962 A1 | 7/2007 | Edie et al. |
| 2008/0071284 A1 | 3/2008 | Lechmann et al. |
| 2008/0133015 A1 | 6/2008 | Lechmann et al. |
| 2015/0173913 A1 | 6/2015 | Lechmann et al. |
| 2015/0223943 A1 | 8/2015 | Lechmann et al. |
| 2018/0055653 A1 | 3/2018 | Lechmann et al. |

FOREIGN PATENT DOCUMENTS

| | | | |
|---|---|---|---|
| FR | 2 836 373 A1 | 8/2003 |
| WO | 97/23174 A1 | 7/1997 |
| WO | 97/37619 A1 | 10/1997 |
| WO | 00/66044 A1 | 11/2000 |
| WO | 00/74605 A1 | 12/2000 |
| WO | 01/56513 A1 | 8/2001 |
| WO | 02/078514 A2 | 10/2002 |
| WO | 03/071992 A2 | 9/2003 |

OTHER PUBLICATIONS

International Search Report for Application No. PCT/CH2004/000250 dated Dec. 28, 2004 (6 pages).

International Preliminary Report on Patentability for Application No. PCT/CH2004/000250 dated Jun. 29, 2006 (14 pages).

U.S. Appl. No. 11/587,722—Non Final Office Action dated Jun. 23, 2009.

U.S. Appl. No. 11/587,722—Amendment in Response to Non Final Office Action.

U.S. Appl. No. 11/587,722—Final Office Action dated Jan. 25, 2010.

European Office Action for Application No. 04729392.3, dated Mar. 13, 2018 (6 pages) (DE only; no English translation available).

* cited by examiner $$S_R = F_1 + F_2 + F_3$$

$$S_L = F_4 + F_5$$

INTERVERTEBRAL PROSTHESIS OR DISK PROSTHESIS

CROSS-REFERENCE TO RELATED APPLICATIONS

This application is a continuation of U.S. application Ser. No. 14/638,196, filed on Mar. 4, 2015, which is a continuation of U.S. application Ser. No. 11/587,723, filed on Sep. 4, 2007, which is a national stage entry pursuant to 35 U.S.C. § 371 of International Application No. PCT/CH04/00250. Each of the above applications is hereby incorporated herein by reference in its entirety.

FIELD

The invention relates to an intervertebral prosthesis or disk prosthesis, especially for arthrodesis surgery by means of dorsal access PLIF (posterior lumbar interbody fusion), TLIF (transforaminal lumbar interbody fusion), ELIF (extraforaminal lumbar interbody fusion), ALIF (anterior lumbar interbody fusion) and ACIF (anterior cervical interbody fusion. The objective of this surgical technique is the treatment of a degenerated or otherwise diseased intervertebral disk. The surgeon looks for access to the intervertebral disk through a centrally placed skin incision. Subsequently, he exposes the rear region of the movement segments, especially the laminae and the pedicle entry points. By means of a partial resection of the facettal and laminar components, the surgeon aims past the nerve roots and the medullary space in the direction of the diseased intervertebral disk.

BACKGROUND

For this surgical technique, only a limited amount of autologous spongiosa is available for filling the cavities of cage-like intervertebral or disk prosthesis and the spaces between individual implants and their surroundings. In the long term, the arthrodesis takes place not with the implant but between the bone and the bone replacement material. The individual implants therefore function only as place holders or spacers.

The intervertebral spaces, supplied with the known intervertebral implants, therefore frequently do not attain complete arthrodesis, that is, they end in a pseudoarthrosis. The situation is much the same also with cage-like intervertebral implants for the cervical spine, as well as for those, which were inserted through ventral entrances. Such intervertebral spaces are not stable mechanically, as would have been expected from a stiffening. The consequences then may be recurring pain with subsequent revision surgery.

For the implants and surgical techniques described above, the surgeon uses autologous bone material, which he obtains from the resected parts of the vertebral body or by means of an additional intervention in the crest of the ilium. Since dorsal accesses to the intervertebral disk space are very narrow, the applying of bone material is made difficult. The surgeon is unable to ensure that the whole of the intervertebral space is filled with autologous bone material. There is therefore the danger that empty spaces will result which, on the one hand, permits migration of the implant. On the other hand, the spaces, not filled with autologous bone material, are filled by a soft, fibrous tissue.

SUMMARY

It is an object of the invention to provide an intervertebral prosthesis or a disk prosthesis, which makes an asymmetric emergence of the osteocementum possible, so that individual regions between the vertebral bodies (for example the central and posteriors zones) are automatically supplied with more osteocementum than other regions.

This objective is accomplished by an intervertebral prosthesis or disc prosthesis, for which the outlet openings are dimensioned differently in size. The amount of osteocementum $K_L$, emerging through $S_L$ is either larger or smaller than the amount of osteocementum $K_R$ emerging through $S_R$; or the amount of osteocementum $K_H$, emerging through $S_H$, is larger or smaller than the amount of osteocementum $K_V$ emerging through $S_V$.

In other words, the outlet openings are dimensioned so that, when flowable osteocementum is supplied through the inlet opening into the cavity, the amount of osteocementum $K_L$ emerging through $S_L$ is either larger or smaller than the amount of osteocementum $K_R$ emerging through $S_R$ or the amount of osteocementum $K_H$, emerging through $S_H$, is larger or smaller than the amount of osteocementum $K_V$, emerging through $S_V$.

The invention permits the intervertebral space to be filled with synthetic bone material (osteocementum) after the cage-like intervertebral prosthesis or disk prosthesis has been placed. The implant is secured by the emergence and subsequent curing of the flowable, hydraulic osteocementum. Due to the asymmetric arrangement of the outlet openings in the implant, the osteocementum can be spread selectively. The inventive prosthesis furthermore has the advantage that it makes superfluous the additional removal of bone at the crest of the iliac, which can cause long enduring pain.

In a special embodiment, the inlet opening is provided in the front side of the prosthesis and the cavity extends from the inlet opening in the direction of the rear side.

In the case of a further embodiment, the inlet opening is disposed in the left all right side of the prosthesis and the cavity extends from the inlet opening in the direction of the opposite right or left side.

In the case of a further embodiment, the cross section of the cavity decreases at least on a partial section as the distance from the inlet opening increases. Due to the tapering of the cavity, the liquid cement mixture flows more easily through the side openings of the implant. The wall of the implant in the opening opposite the injection point has a shearing-off edge, so that the liquid cement mixture is diverted.

In the case of a further embodiment, the cavity tapers, at least on a partial section, either in wedge-shaped or conical fashion. In the case of a further embodiment, the upper and lower sides converge in the direction of the front side at least on a partial section. In yet another embodiment, the prosthesis is filled at least partially with a cured hydraulic osteocementum, which extends at least partially beyond the outlet opening.

In the case of a further embodiment, the implant may consist of two intervertebral prostheses, which are disposed next to one another, the right side of the intervertebral prosthesis disposed on the left being oriented in the direction of the left side of the intervertebral prosthesis disposed on the right. For the intervertebral prosthesis disposed on the left, the condition $S_L > S_R$ applies and for the intervertebral prosthesis on the right, the condition $S_R > S_L$.

Moreover, the intervertebral prosthesis may be varied in many ways, for example, by using flat, concave, convex or also spherical side walls.

Calcium phosphate cements, which, after the two components are mixed, may be injected in liquid form into the implant and are subsequently cured hydraulically, are suitable as flowable hydraulic osteocementum.

BRIEF DESCRIPTION OF THE DRAWINGS

The invention and further development of the invention are described in even greater detail by means of several examples and partially diagrammatic drawings, in which.

DETAILED DESCRIPTION OF THE PREFERRED EMBODIMENTS

Figure 1:
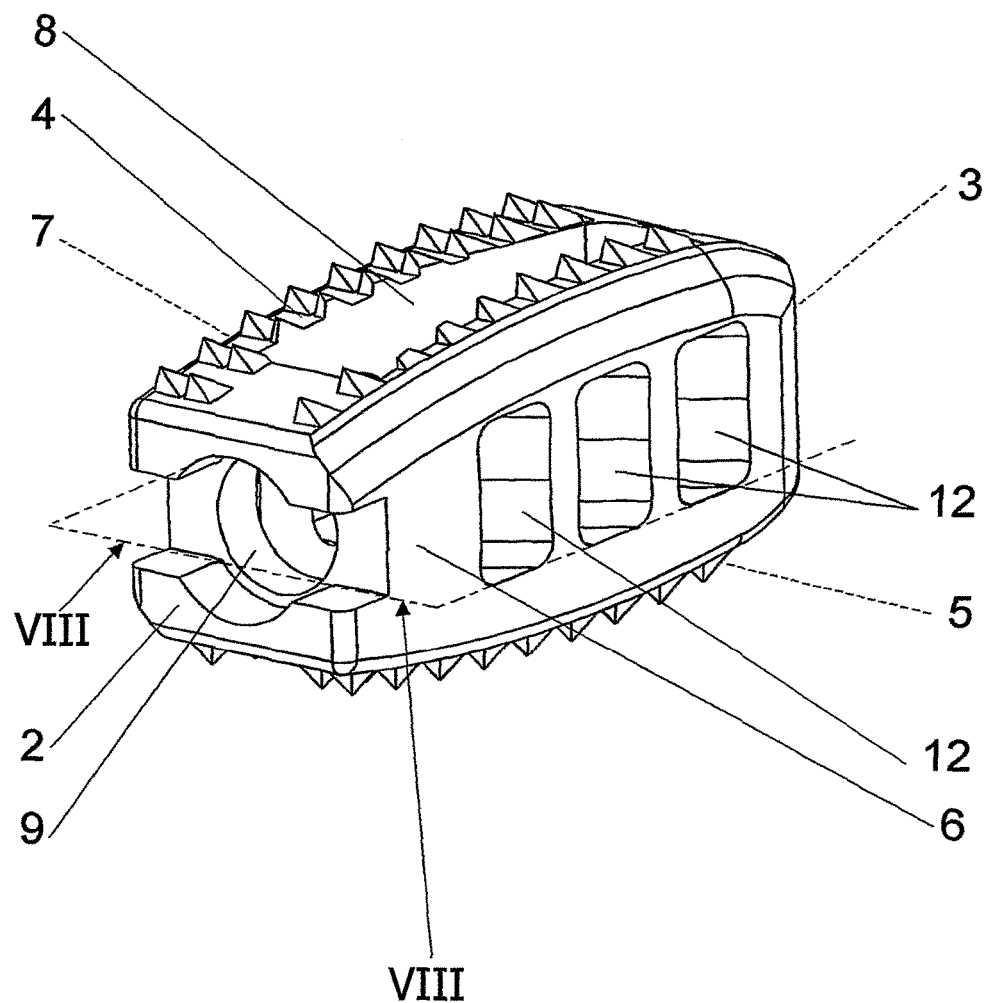
FIG. 1 shows a perspective view of an inventive, lens-shaped intervertebral implant.
Figure 2:
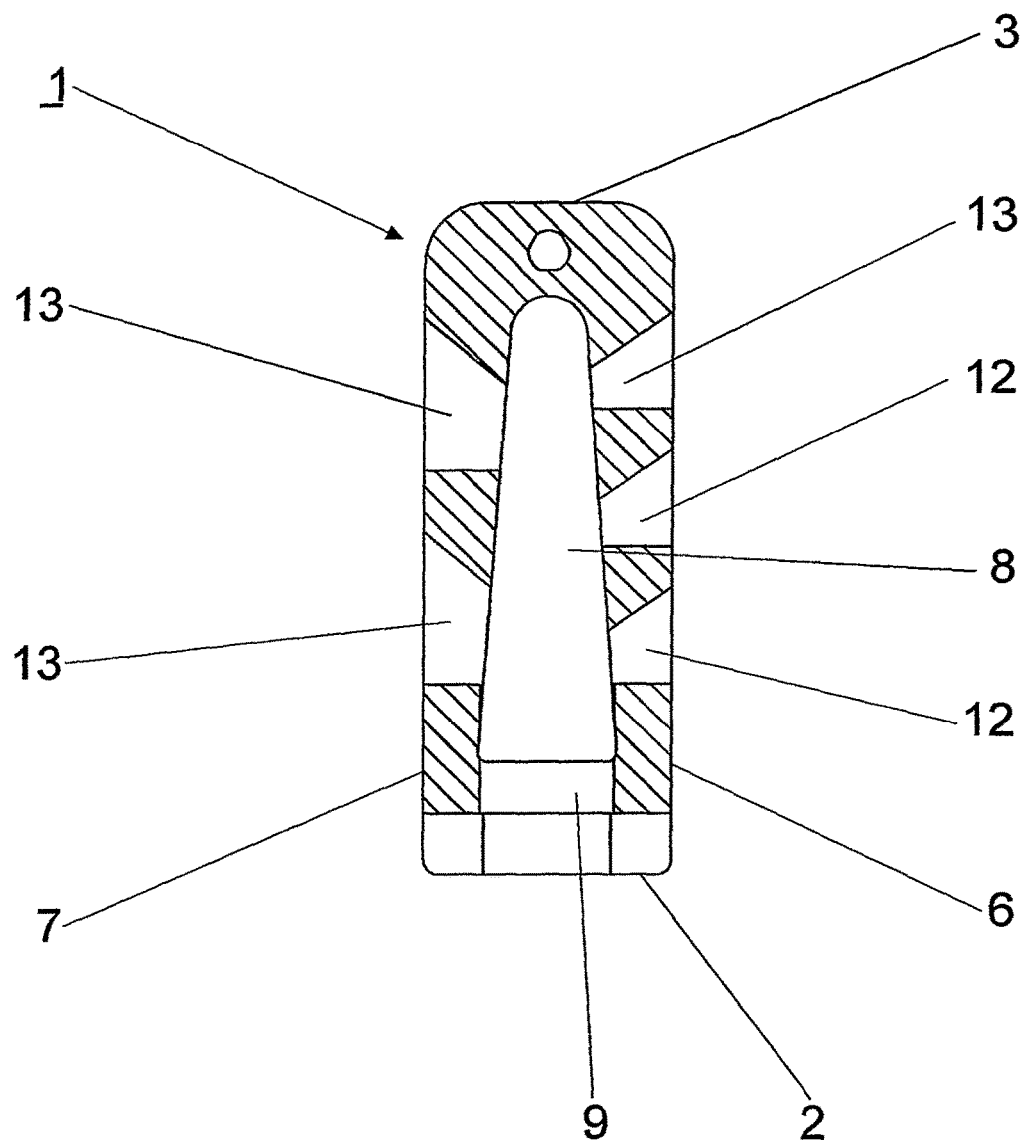
FIG. 2 shows a longitudinal section through the intervertebral implant of FIG. 1 along the central plane VIII-VIII.

The intervertebral prosthesis 1, shown in FIGS. 1 and 2, consists of a rectangular hollow body and has a front side 2, a rear side 3, an upper side 4 suitable for positioning against the baseplate of a vertebral body, a lower side 5 suitable for positioning against the baseplate of a vertebral body, a right side 6, a left side 7, a cavity 8 suitable for accommodating a flowable, hydraulic osteocementum, an inlet opening 9 into the cavity 8 and several outlet openings 10; 11; 12; 13 from the cavity 8. The upper side 4 and the lower side 5 converge toward the front side 2 as well as toward the rear side 3, so that a lens-like configuration of the intervertebral prosthesis results.

As can be seen from FIG. 2, the cross section of the cavity 8 decreases in the shape of a cone as the distance from the inlet opening 9 increases.

Figure 3:
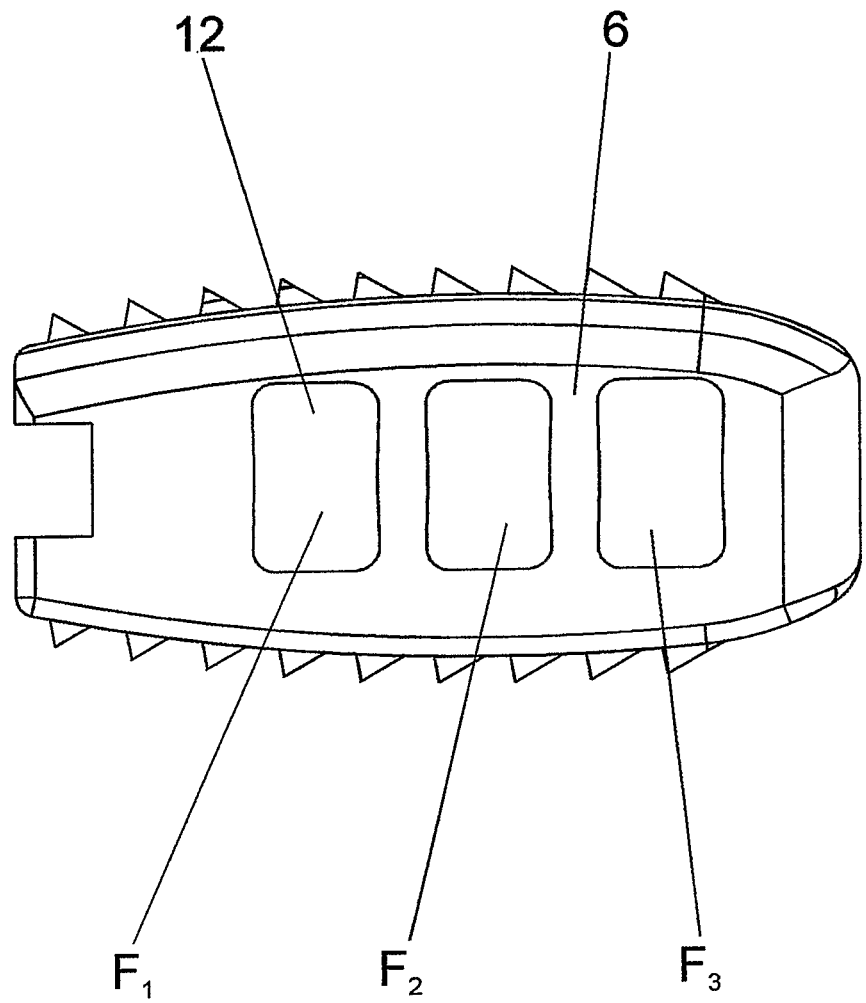
FIG. 3 shows a side view from the right of the intervertebral implant of FIG. 1.

As shown in FIG. 3, there are three outlet openings 12 with areas $F_1$, $F_2$ and $F_3$ in the right side 6 of the intervertebral prosthesis 1, so that the sum $S_R$ of the cross sectional surfaces of the outlet openings emerging the right side 6 is $S_R = F_1 + F_2 + F_3$.

Figure 4:
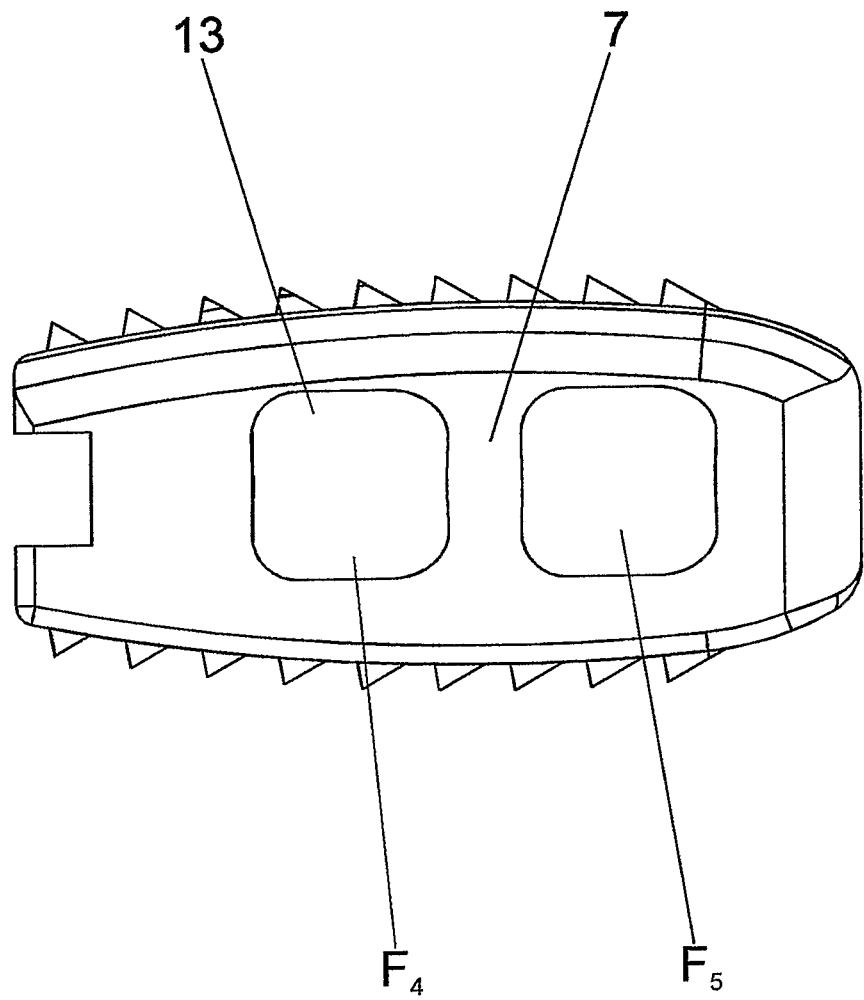
FIG. 4 shows a side view from the left of the intervertebral implant of FIG. 1.

As shown in FIG. 4, there are two outlet openings 13 with the areas $F_4$ and $F_5$ in the left side 7 of the intervertebral prosthesis 1, so that the sum $S_L$ of the cross-sectional surfaces of the outlet openings emerging for the left side 7 is $S_L = F_4 + F_5$.

It is important that the sum $S_L > S_R$, so that more osteocementum can emerge on the left side 7 of the intervertebral prosthesis 1 from the cavity 8 through the outlet opening 13 into the intervertebral space than from the right side 6.

Figure 5:
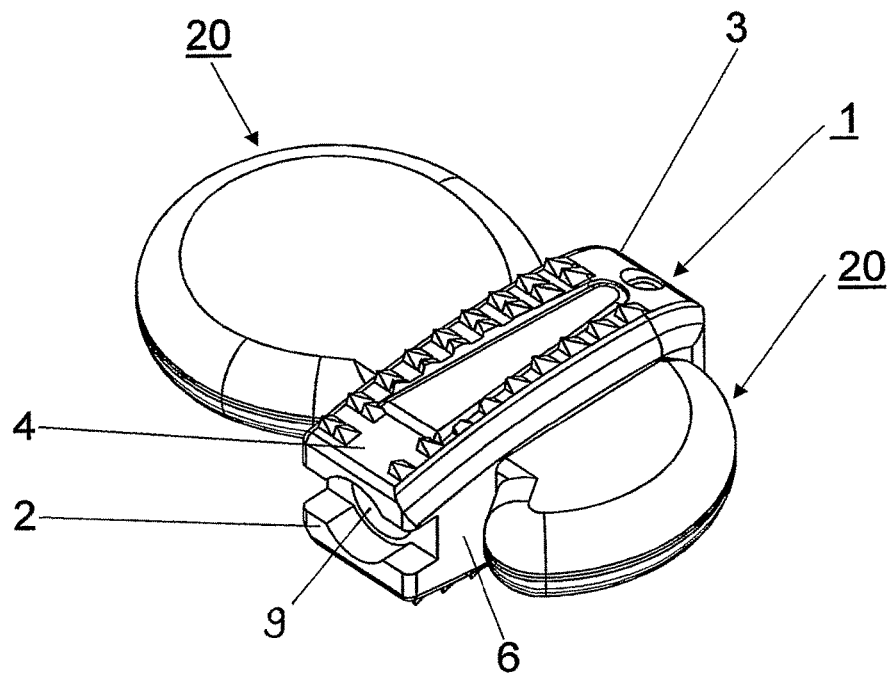
FIG. 5 shows a perspective view of an inventive intervertebral prosthesis, which is secured by means of cured osteocementum.
Figure 6:
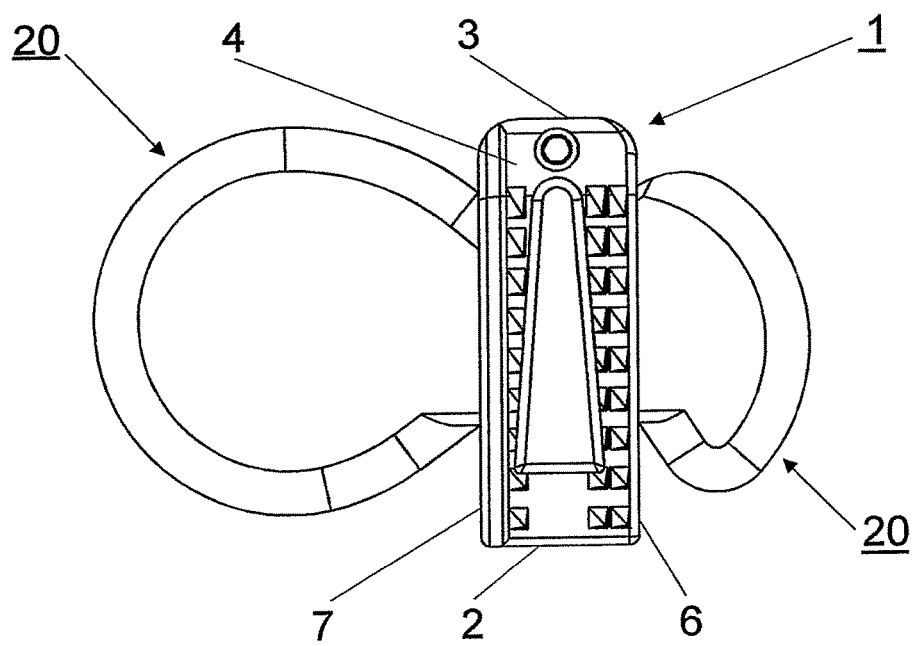
FIG. 6 shows a plan view of the intervertebral prosthesis of FIG. 5.

FIGS. 5 and 6 show how the osteocementum 20, emerging from the right side 6 and the left side 7 of the intervertebral prosthesis 1, is distributed. Because the sum $S_L$ of the cross sectional areas of the outlet openings 13 emerging on the left side 7 is larger, the amount of osteocementum 20, emerging on the left side 7 and curing, is also larger than that emerging on the right side 6 and curing.

Figure 7:
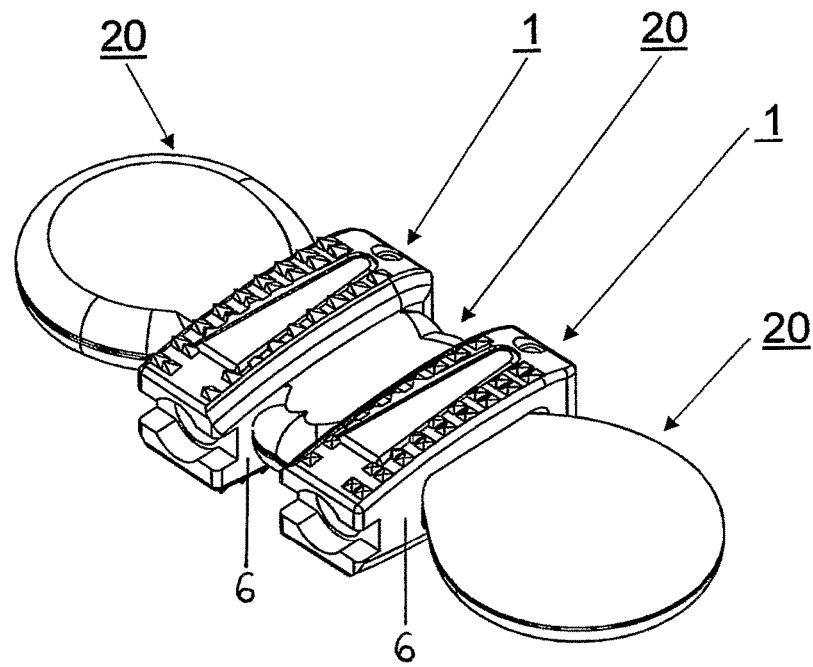
FIG. 7 shows a perspective view of a variation of the embodiment, using two intervertebral implants, the osteocementum securing the implant in their position relative to one another as well as to prevent migrating apart.
Figure 8:
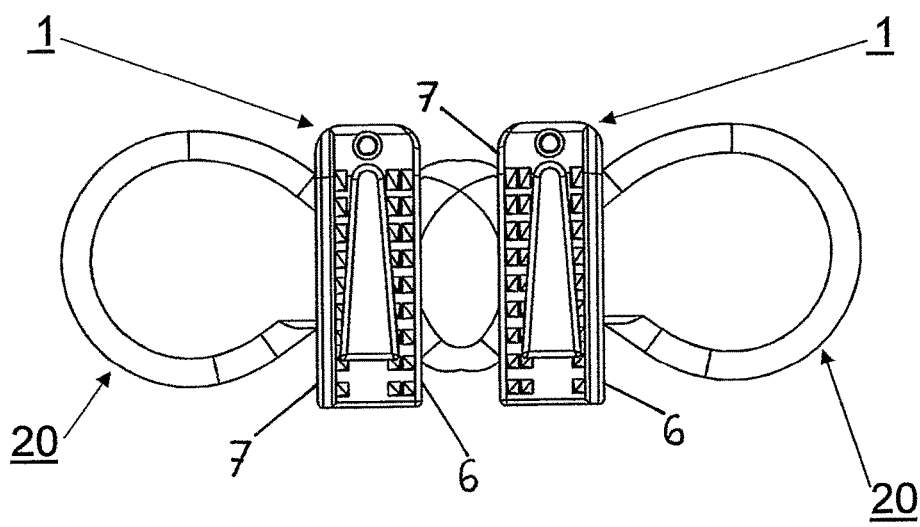
FIG. 8 shows a plan view of the two intervertebral implants of FIG. 7.

FIGS. 7 and 8 show a further embodiment, which consists of two inventive intervertebral prosthesis 1, which are disposed next to one another. The two intervertebral prostheses are positioned in such a manner, that the right side 6 of the intervertebral prosthesis 1, which is disposed on the left, is oriented in the direction of the left side 7 of the intervertebral prosthesis 1, which is disposed on the right. For the intervertebral prosthesis 1, disposed on the left, the condition $S_L > S_R$ applies, whereas, for the intervertebral prosthesis 1, which is disposed on the right, the reverse applies, namely $S_R > S_L$. Due to this measure, less osteocementum 20 emerges in the space between the two intervertebral prostheses 1 than emerges to the right side of the intervertebral prosthesis 1 disposed on the right and to the left side 7 of the intervertebral prosthesis 1 disposed on the left.

Figure 9:
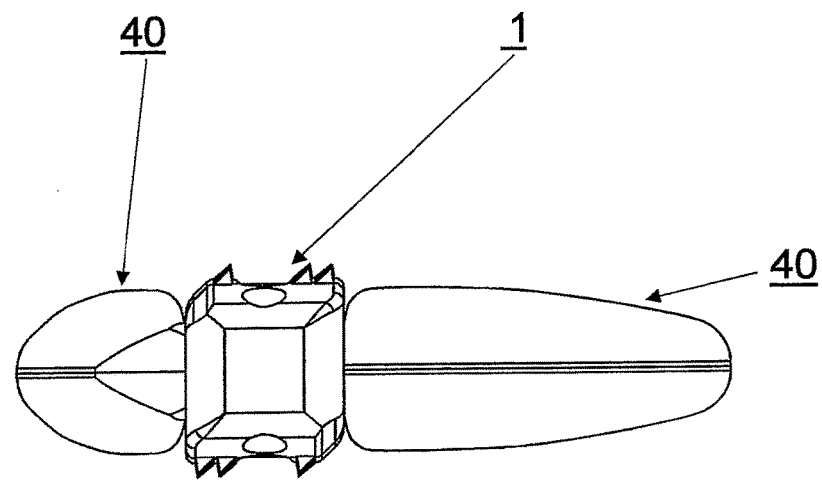
FIG. 9 shows a front view of a variation of the embodiments, in which the perforated intervertebral implant has a rectangular cross section

FIG. 9 shows a variation of the embodiment of an inventive intervertebral implant 1, which has a rectangular cross section and from which a larger amount of osteocementum 40 has emerged on the right side than on the left side.

Figure 10:
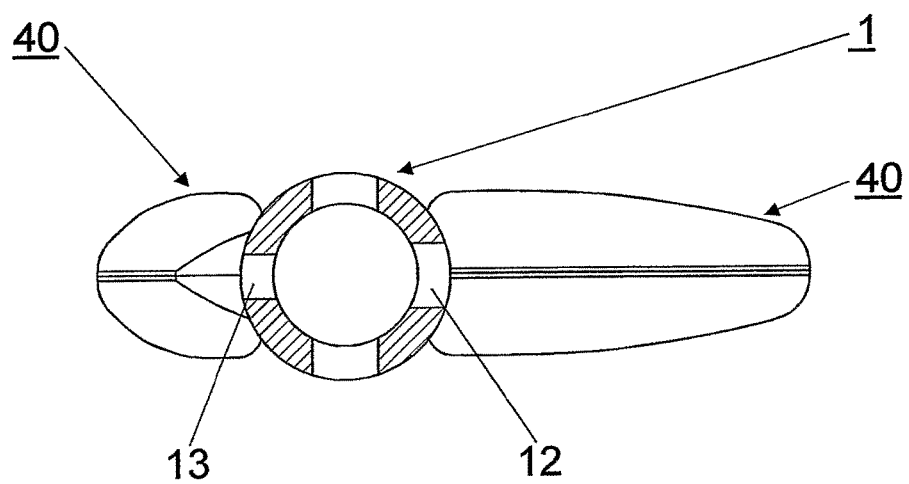
FIG. 10 shows a front view of a variation of the embodiment, in which the perforated intervertebral implant has a circular ring-shaped cross section.

FIG. 10 shows a further variation of an embodiment of an intervertebral prosthesis 1, which has a circular cross section and for which the amount of osteocementum 40 emerging on the right side through the outlet openings 12 is larger than that emerging on the left side through outlet openings 13.

The invention claimed is:

1. A surgical method comprising:
   implanting an intervertebral implant between an upper vertebra and a lower vertebra, wherein the intervertebral implant includes:
   a cavity defined by a body having a first end engaged with a delivery tool, the first end having an inlet opening for receiving a flowable material;
   a top surface in contact with at least a portion of the upper vertebra;
   a bottom surface in contact with at least a portion of the lower vertebra;
   a second end opposite the first end;
   a first lateral side being substantially straight and having a first length extending between the first and second ends, a first height extending between the top and bottom surfaces, and at least one opening; and
   a second lateral side being substantially straight and having a second length extending between the first and second ends, a second height extending between the top and bottom surfaces, and at least one opening,
   wherein the first length is substantially the same as the second length and the first height is substantially the same as the second height, and
   conveying a volume of flowable material to the intervertebral implant using the delivery tool, such that the flowable material flows asymmetrically out of the implant and into a surrounding disc space defined between the upper and lower vertebrae.

2. The method of claim 1, wherein:
   the at least one opening of the first lateral side has a combined cross-sectional area A1;

the at least one opening of the second lateral side has a combined cross-sectional area A2; and A1 is not equal to A2 thereby providing that the flowable material emerges asymmetrically from the implant through said openings.

3. The method of claim 2, wherein A1 is greater than A2 so that the volume of flowable material emerging through the first side is greater than the volume of flowable material emerging through the second side.

4. The method of claim 1, wherein the cavity extends from the inlet opening towards the second end.

5. The method of claim 1, wherein the implant has a rectangular cross section.

6. The method of claim 1, wherein a cross-sectional area of the cavity decreases as the distance from the inlet opening increases.

7. The method of claim 1, wherein a cross-sectional area of the cavity decreases in one of a wedge-shape or a conical shape.

8. The method of claim 1, wherein the top surface and the bottom surface converge towards the second end.

9. The method of claim 1, wherein the flowable material comprises osteocementum.

10. A surgical method comprising:
placing an implantable intervertebral cage in a disc space defined between an upper vertebra and a lower vertebra, wherein the cage includes:
  a first end engaged with a delivery tool, the first end having an inlet opening for receiving flowable material;
  a second end opposite the first end, the second end being closed so that flowable material cannot emerge therefrom;
  a top surface in contact with at least a portion of the upper vertebra;
  a bottom surface in contact with at least a portion of the lower vertebra; and
  first and second substantially straight sidewalls having equal lengths and having at least one opening formed therein through which flowable material can emerge from the cage; and
delivering flowable material to a cavity of the cage using the delivery tool such that the flowable material delivered to the cavity flows asymmetrically out of the cage and into the surrounding disc space.

11. A surgical method comprising:
placing an implantable intervertebral cage in a disc space defined between an upper vertebra and a lower vertebra, wherein the cage includes:
  a first end engaged with a delivery tool, the first end having an inlet opening for receiving flowable material;
  a second end opposite the first end, the second end being closed so that flowable material cannot emerge therefrom;
  a top surface in contact with at least a portion of the upper vertebra;
  a bottom surface in contact with at least a portion of the lower vertebra; and
  first and second substantially straight sidewalls having equal lengths and having at least one opening formed therein through which flowable material can emerge from the cage; and
delivering flowable material to a cavity of the cage using the delivery tool such that a greater amount of flowable material emerges from the cage into a first lateral portion of the disc space than into a second lateral portion of the disc space opposite to the first lateral portion.

12. The method of claim 11, wherein:
the at least one opening of the first lateral side has a combined cross-sectional area A1;
the at least one opening of the second lateral side has a combined cross-sectional area A2; and
A1 is not equal to A2 thereby providing that the flowable material emerges asymmetrically from the implant through said openings.

13. The method of claim 12, wherein A1 is greater than A2 so that the volume of flowable material emerging through the first sidewall is greater than the volume of flowable material emerging through the second sidewall.

14. The method of claim 11, wherein the cavity extends from the inlet opening towards the second end.

15. The method of claim 11, wherein the cage has a rectangular cross section.

16. The method of claim 11, wherein a cross-sectional area of the cavity decreases as the distance from the inlet opening increases.

17. The method of claim 11, wherein a cross-sectional area of the cavity decreases in one of a wedge-shape or a conical shape.

18. The method of claim 11, wherein the flowable material comprises osteocementum.

* * * * *